United States Patent [19]

Dessau et al.

[11] Patent Number: 4,830,729

[45] Date of Patent: May 16, 1989

[54] DEWAXING OVER CRYSTALLINE INDIUM SILICATES CONTAINING GROUPS VIII MEANS

[75] Inventors: Ralph M. Dessau, Edison, N.J.; Ernest W. Valyocsik, Yardley, Pa.; Chaya Venkat, Princeton, N.J.

[73] Assignee: Mobil Oil Corporation, New York, N.Y.

[21] Appl. No.: 138,462

[22] Filed: Dec. 28, 1987

[51] Int. Cl.$^4$ ............................................. C10G 65/04
[52] U.S. Cl. ...................... 208/89; 208/109; 208/110; 208/27; 208/134; 208/138; 208/18; 585/407
[58] Field of Search .............. 208/120, 118, 119, 121, 208/122, 18, 24, 89, 111, 109, 110, 138, 134, 27; 502/64, 84; 585/407, 411

[56] References Cited

U.S. PATENT DOCUMENTS

| | | | |
|---|---|---|---|
| 3,702,293 | 11/1972 | Hayes et al. | 208/139 |
| 3,702,294 | 11/1972 | Rausch | 208/139 |
| 3,878,131 | 4/1970 | Hayes | 252/466 PT |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,439,310 | 3/1984 | Audeh et al. | 208/120 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,652,360 | 3/1987 | Dessau | 208/138 |
| 4,668,377 | 5/1987 | Chen et al. | 208/111 |
| 4,699,708 | 10/1987 | Dessau | 208/111 |
| 4,704,495 | 11/1987 | Dessau | 585/419 |

FOREIGN PATENT DOCUMENTS

| | | | |
|---|---|---|---|
| 0074651 | 3/1983 | European Pat. Off. | 502/64 |
| 0107389 | 4/1984 | European Pat. Off. | 502/64 |
| 3115324 | 11/1982 | Fed. Rep. of Germany | 502/74 |
| 2520636 | 1/1983 | France | 585/434 |
| 7609102 | 8/1976 | Netherlands | 208/141 |
| 8202272 | 1/1984 | Netherlands | 585/419 |
| 2033358 | 5/1980 | United Kingdom | 502/64 |
| 2114150 | 8/1983 | United Kingdom | 208/138 |

OTHER PUBLICATIONS

Haag et al., "The Active Site of Acidic Aluminosilicate Catalysts", Nature vol. 309, pp. 589–591 (1984).

"Indium Oxide Treated H-ZSM-5 Catalyst, Properties and Catalytic Activity in the Methanol Conversion", Leon W. Zatorski, Bulletin of the Polish Academy of Sciences, Chemistry, vol. 35, No. 7–8, 1987.

G. Wengui et al. "IR Study of Framework Vibrations and Surface Properties of High Silica Zeolites", Zeolites, Elsevir Science, Amsterdam, 1985, p. 279 Ione, Journal of Molecular Catalysis, 31, pp. 355–370 (1985).

Ione, "Structure and Reactivity of Modified Zeolites", Elsevir Science, (1984), pp. 151–155.

Huagong, vol. 15, No. 7 (1986) (with translation).

*Primary Examiner*—Anthony McFarlane
*Attorney, Agent, or Firm*—Alexander J. McKillop; Charles J. Speciale; Marina V. Schneller

[57] ABSTRACT

Catalytic dewaxing of wax containing hydrocarbon feedstocks is undertaken in the presence of a catalyst composition comprising a dehydrogenation metal in combination with a non-acidic microporous crystalline material to maximize liquid yield.

9 Claims, No Drawings

DEWAXING OVER CRYSTALLINE INDIUM SILICATES CONTAINING GROUPS VIII MEANS

FIELD OF THE INVENTION

The invention pertains to catalytic dewaxing of waxy feedstocks by a catalytic composition comprising a dehydrogenation metal, such as platinum, in combination with a non-acidic crystalline microporous indium containing material. Liquid yields of product are maximized by substantially reducing cracking of the wax components during dewaxing. The dewaxed product has a pour point less than that of the feed.

BACKGROUND OF THE INVENTION

The art recognizes several methods for eliminating the waxy component(s) of waxy feeds, generally referred to as dewaxing. Solvent refining was, and is still currently, a method by which wax is removed from waxy feedstocks. The use of solvent is both cumbersome and expensive, because of the volume of feed to be processed, and the inherent expense of solvent.

Catalytic cracking and hydrocracking treatments may be used to reduce the wax content of feedstocks. The wax content of feedstocks is attributable to long chain unbranched and slightly branched aliphatics. Accordingly, catalytic cracking (and hydrocracking) of the wax components reduces the liquid volume of product vis-a-vis that of the feed. Moreover, alteration of other components of the feed occurs.

The problems which inhere in those dewaxing processes are in large part due to the complexity of the molecular constitution of the feeds. Accordingly, empirical considerations control dewaxing processing techniques.

SUMMARY OF THE INVENTION

By employing a non-acidic catalyst in dewaxing, substantial reduction and/or elimination of products of cracking and hydrocracking are realized. Accordingly, compared to catalytic dewaxing in the presence of acidic catalysts, liquid yields are increased. Off-gas, biproduct(s) of cracking (and hydrocracking) are also substantially reduced and/or eliminated.

By employing the catalyst of the dewaxing process of the invention, the nature of the products resulting from conversion of the wax components is predictable. In accordance with the invention, the wax components are converted to distillate range products. Under catalytic dewaxing conditions, the contact of a wax containing feedstock with a catalyst comprising a dehydrogenation metal and a non-acidic crystalline microporous indium containing material achieves the foregoing results.

DETAILED DESCRIPTION OF THE INVENTION

In accordance with the invention, wax content of waxy feedstocks is decreased, under dewaxing conditions, by contact with a catalyst comprising a dehydrogenation/hydrogenation metal and a non-acidic, microporous crystalline indium containing material. In this catalytic process the wax components of the waxy feed stock are converted to distillate boiling range products, the pour point of the feed is reduced; and liquid yields, are maximized with low, if any, gas production.

Feeds

Waxy hydrocarbon oils boiling within the range of about 350° to 1025° F. may be treated in accordance with the invention. Gas oils, kerosenes, vacuum gas oils, whole crudes and oils derived from tar sands, shale and coal are contemplated for use herein.

The term "waxy", as used herein will refer to an oil of sufficient wax content to result in a pour point greater than 0° F., and preferably greater than +30° F. Components of the feed which render the feed waxy include straight chain normal or slightly branched paraffins. This process of the invention converts the waxy long chain paraffins into materials which are compatible with the oil product, e.g., fuel oil product, permitting increased yields of oil. From a liquid yield standpoint, it is much more beneficial, to convert long chain paraffins to other liquid products than it is to simply crack or hydrocrack to light gases.

In accordance with the invention, the $C_{15}+$ long chain normal or slightly branched chain aliphatics are converted to distillate range products, and thus the resultant product has a reduced pour point, as well as a reduced wax content.

Prior to dewaxing, the feeds may have been hydrotreated. Initial hydrotreating of a hydrocarbon feed serves to convert sulfur, nitrogen and oxygen derivatives of hydrocarbons to hydrogen sulfide, ammonia and water while depositing metal contaminant from hydrodecomposition of any organo-metal compounds. Where desired, interstage processing of the effluent from the hydrotreating zone may be effected. Such interstage processing may be undertaken, for example, to provide additional hydrogen, to add or remove heat or to withdraw a portion of the hydrotreated stream. Hydrotreating may be essential. Suitable, the temperature in the hydrotreating catalyst bed will be within the approximate range of 550° F. to 850° F. The feed is conducted through the bed at an overall space velocity between about 0.1 and about 10 and preferably between about 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon (feed).

The catalyst may be any of the known hydrotreating catalysts, many of which are available as staple articles of commerce. These hydrotreating catalysts are generally metals or metal oxides of Group VIA and/or Group VIII deposited on a solid porous support, such as silica and/or metal oxides such as aluminas, titania, zirconia or mixtures thereof. Representative Group VIA metals include molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent.

Dewaxing Conditions

In accordance with the invention, the waxy feedstock is contacted under dewaxing conditions with a catalyst composition comprising a dehydrogenation/hydrogenation metal and an indium containing non-acidic crystalline microporous material.

The dewaxing conditions are tabulated below:

| Dewaxing Conditions | |
| --- | --- |
| Pressure, broad, (psig) | 0–1000 |
| Pressure, preferred (psig) | 20–500 |
| Temperature, broad (°F.) | 500–1200 |
| Temperature, preferred (°F.) | 800–1050 |
| WHSV* | 0.1–20 |
| WHSV, preferred | 0.2–10 |
| H$_2$:oil | 0–20:1 |

*WHSV = weight hourly space velocity, weight of feed per unit weight of catalyst per hour.

The Dewaxing Catalyst

The dewaxing catalyst comprises a dehydrogenation/hydrogenation metal and a non-acidic crystalline microporous indium containing material.

The amount of dehydrogenation/hydrogenation metal in the catalyst can range from 0.01 to 30 weight percent and practically from 0.1 to 10 weight percent. The dehydrogenation/hydrogenation metal can be any Group VIII metal, chromium or vanadium; preferably, it is a platinum group metal and most preferably it is platinum.

The indium content of the crystalline materials can range from 0.01 to 20 weight percent. Practically, the indium content will range from 0.1 to 10 weight percent.

The crystalline indium containing materials of the invention include zeolites characterized by Si/Al ratios of at least 2. However, the silica:alumina ratio of the zeolite can be up to 1000, or greater. In specific embodiments the aluminum content of some of these materials is less than 0.1 weight percent.

The crystalline indium containing material of the invention can contain other elements including boron, iron, chromium and gallium. The content of these other elements in the crystalline indium containing material can range from 0 to 10 weight percent.

The indium containing precursors of the invention, described herein, are crystalline in the sense that they are identifiable as isostructural with zeolites by X-ray powder diffraction pattern.

The crystalline microporous indium containing material has an X-ray diffraction pattern which corresponds to a zeolite, SAPO, ALPO, etc. For example, indium silicate compositions of the invention have been made the crystal structure of which is that of ZSM-5, ZSM-11, ZSM-12, ZSM-20, ZSM-23, ZSM-48, ZSM-50, zeolite Beta, and SAPO-5; the X-ray diffraction pattern and significant lines Tables of these materials have been described in the U.S. Patent literature. These are characterized by pore sizes up to about 8 Angstroms. In a preferred embodiment the pore size of the microporous crystalline indium containing silicates ranges from about 5 to about 8 Angstroms.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimension of 0.1 micron):

1. Small pore: n-C$_6$/i-C$_6$ sorption ratio greater than approximately 10.
2. Medium pore: n-C$_6$/i-C$_6$ is less than 10 and n-C$_6$/Mesitylene sorption ratio greater than approximately 5.
3. Large pore: n-C$_6$/Mesitylene sorption ratio less than approximately 5.

The compositions comprising hydrogenation/dehydrogenation metal combined with the crystalline indium containing materials do not exhibit any appreciable acid activity. These catalysts would meet the criteria of non-acidic catalysts described by Davis and Venuto, J. CATAL. Vol. 15, p. 363 (1969). Thus, a non-equilibrium mixture of xylenes are formed from either n-octane or each individual methylheptane isomer, with the octane yielding more o-xylene and 2-methyl-heptane yielding mostly m-xylene, at conversions between and 10 and 60%. Alternatively, the non-acidic compositions will exhibit a pH of at least 6 when added to distilled deionized pH7 water maintained under inert (such as argon) atmosphere; by an inert atmosphere in this context it means an atmosphere free of CO$_2$. Typically, in these tests, 100 mg of catalyst was added to 30 ml. of distilled deionized water. Some compositions will exhibit a pH of at least 7.5 depending on the metal content.

When, as in embodiments herein, the crystalline indium dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison indium-free counterparts of those compositions catalyzed also hydrogenolysis of paraffins, e.g., to methane, as a major competing side reaction; and, accordingly, the latter compositions exhibit decreased selectivity for the aromatization of paraffins but increased selectivity for C$_1$–C$_5$ paraffin production. Some of the aforementioned catalysts were screened for hexane and heptane aromatization at 538° C. in the presence of nitrogen diluent. The results are shown in Table A below in which the crystalline silicate employed exhibited the diffraction pattern of a ZSM-5.

TABLE A

Paraffin Aromatization over Pt/ZSM-5

| Support | Paraffin | Conversion | Benz. Sel.[c] | Tol. Sel. | C5-Sel |
|---|---|---|---|---|---|
| B/ZSM-5 | n-hexane | 52% | 31% | — | 12%[a] |
| " | n-hexane | 98% | 51% | 2% | 40%[a] |
| " | heptane | 56% | 56% | 8% | 7%[a] |
| " | heptane | 95% | 33% | 31% | 34%[a] |
| In/ZSM-5 | n-hexane | 60% | 81% | — | 1% |
| In/ZSM-5 | n-hexane | 99+% | 95% | — | 4% |
| In/ZSM-5 | heptane | 50% | — | 92% | 1% |
| In/ZSM-5 | heptane | 99% | — | 97% | 1% |
| Si/ZSM-5[b] | n-hexane | 58% | 69% | — | 18%[a] |
| Si/ZSM-5[b] | n-hexane | 99% | 72% | — | 26%[a] |
| Si/ZSM-5[b] | heptane | 34% | 45% | 17% | 14%[a] |
| Si/ZSM-5[b] | heptane | 99% | 62% | 4% | 34%[a] |

[a] primarily methane.
[b] high silica/alumina ZSM-5.
[c] $H_2$—free selectivity based on carbon.

The non-acidic platinum catalyst prepared from In/ZSM-5 provided much higher aromatics selectivity than all the other catalysts examined. Benzene yields from hexane were as high as 95%, while heptane produced toluene in 97% yield ($H_2$ free carbon base).

The other catalysts, including Pt/B-ZSM-5 and Pt/high silica:alumina ratio did not show any appreciable acid activity, in that platinum chemistry dominated. Significant metal-catalyzed aromatization was observed; however hydrogenolysis to methane constituted a major competing side reaction. The highest toluene selectivity observed was 50-55%, and in most cases that selectivity was significantly lower. This is in sharp contrast to the aromatic product selectivity of the platinum-/In/ZSM-5. The cause for this difference in platinum behavior from the Pt/In-ZSM-5 catalyst is not clear.

Synthesis of the Compositions

The crystalline microporous indium-materials can be made in various ways. Indium incorporation can be during synthesis or post-synthesis; and the materials can be prepared either by stepwise or simultaneous incorporation of the indium and the hydrogenation/dehydrogenation function. Stepwise preparation includes techniques of cocrystallization, impregnation, or exchange. Crystallization can be undertaken in a two phase system described in commonly assigned Ser. No. 878,555, filed June 26, 1986. Other elements such as boron, iron chromium, gallium, can also be included. Simultaneous incorporation includes the combination of indium with the dehydrogenation/hydrogenation function during synthesis (i.e., crystallization) or simultaneously after synthesis of the crystalline material.

An indium free material can be treated with indium compounds at elevated temperatures. Such treatments can be conducted so that the source of indium is either in the gaseous (such as indium chloride) or the liquid phase including the aqueous phase (such as indium nitrate). Alternatively, an indium free crystalline reactant can simply be impregnated with indium source and then calcined at temperatures above 400° C.

The indium free material may have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$, $Ca^{++}$, $Mg^{++}$, $Ba^{++}$, $Sr^{++}$ or admixtures thereof. The alkali metals or alkali earth metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

The non-acidic, crystalline, microporous, indium modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica.

The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite.

EXAMPLES

The catalyst employed contained 40.42% Si, 2.88% In, 0.45% Na, 358 ppm Al, and 2.3% Pt and exhibited the X-ray diffraction pattern of ZSM-5. It was produced as described in the Examples below. The "non-acidic" nature of the catalyst was confirmed by its ability to aromatize n-heptane to toluene in high yield. At 500° C. and 30 torr heptane in nitrogen, toluene was formed in 95% yield.

The intrazeolitic nature of the platinum was confirmed by the preferential hydrogenation of hexene-1 in the presence of 4,4-dimethylhexene-1.

Lube dewaxing was undertaken employing a high pour (120° F.) heavy neutral raffinate as feed in the dewaxing experiment. The properties of the feed are listed in Table 1.

TABLE 1

| CHARGE STOCK | | |
|---|---|---|
| H—NMR | PCT | 14.3 |
| NITROGEN-CHEMILUMINESCE | | 7 PPM |
| BASIC NITROGEN-TITN, | | 3 PPM |
| SULFUR BY XRF, 0.002-5% | PCT | 0.02 |
| API GRAVITY | | 31.5 |
| REFRACTIVE INDEX LIQUIDS | | 1.458 |
| FLASH PT CLEVE OPEN CUP | | 505 |
| KINEMATIC VISCOSITY (100° C.) | | 9.648 |
| KINEMATIC VISCOSITY (300° F.) | | 3.991 |
| AROM BY SILICA GEL | | |
| PERCENT RECOVERED | | 83.98 |
| PERCENT RESIDUE | | 15.44 |
| PERCENT LOSS | | 0.58 |
| PERCENT NON-AROMATICS | | 84.47 |
| PERCENT AROMATICS | | 15.53 |
| VACUUM DIST | | |
| IBP | | 714 |
| 5 VOL PERCENT DISTILLED | | 853 |
| 10 VOL PERCENT DISTILLED | | 878 |
| 20 VOL PERCENT DISTILLED | | 890 |
| 30 VOL PERCENT DISTILLED | | 905 |
| 40 VOL PERCENT DISTILLED | | 921 |

TABLE 1-continued

| | |
|---|---|
| 50 VOL PERCENT DISTILLED | 936 |
| 60 VOL PERCENT DISTILLED | 954 |
| 70 VOL PERCENT DISTILLED | 979 |
| 80 VOL PERCENT DISTILLED | 1010 |
| 90 VOL PERCENT DISTILLED | 1053 |
| 95 VOL PERCENT DISTILLED | 1086 |
| PERCENT RECOVERED | 98.0 |
| END POINT | 1126 |

Dewaxing was carried out in a continuous flow microreactor at about 538° C., 200 psig and 0.5 WHSV. The $H_2$:oil ratio was 1.9. The product yields are shown in Table 2 below:

TABLE 2

| Product Yields from Dewaxing | |
|---|---|
| Days on Stream = | 4.8 |
| Lube Yield (650+ F.) = | 62.5% |
| Kerosine Yield (330–650° F.) = | 14.5% |
| Naphtha Yield (125–330° F.) = | 19.0% |
| Total Liquid Yield = | 96.0% |

A chromatogram of the lube and kerosine fraction shows that the waxy paraffins have been converted from the 650° F.+ range into the distillate range. The pour point of the 650° F.+ lube material was 22° F., as compared to the feed pour point of 120° F. Furthermore, shifting the paraffinic material into the distillate range produced a high quality distillate with an estimated cetane number of 55.

EXAMPLE A

Other indium containing non-acidic crystalline microporous materials in combination with a dehydrogenation/hydrogenation metal for use in the invention have been made.

Crystalline silicate products were produced containing indium and exhibiting characteristic X-ray diffraction patterns of structures corresponding to ZSM-5, ZSM-11, ZSM-12, ZSM-23, ZSM-48 and ZSM-50.

Table 1A compiles the composition ranges employed in the synthesis of a series of In/ZSM-5 products with widely varying indium content. Also shown in Table 1A is the synthesis of indium-containing silicates having X-ray pattern of ZSM-11, ZSM-12, ZSM-23, ZSM-48 and ZSM-50. The footnotes in Table 1A specify the $SiO_2$ sources and the organic directing agents employed in the synthesis.

TABLE 1A

Crystallizations of Indium-Containing Zeolites
160° C.; Stirred 400 rpm

| | Mixture Compositions (Mole Ratios) | | | | | | |
|---|---|---|---|---|---|---|---|
| Run No. | $\frac{SiO_2}{In_2O_3}$ | $\frac{H_2O}{SiO_2}$ | $\frac{OH^-}{SiO_2}$ | $\frac{NA^+}{SiO_2}$ | $\frac{R}{SiO_2}$ | Time, Days | Zeolite Product |
| 1[a] | 500 | 48 | 0.26 | 0.27 | 0.10[c] | 3 | ZSM-5 |
| 2[b] | 500 | 48 | 0.26 | 0.27 | 0.10[c] | 3 | ZSM-5 |
| 3[a] | 300 | 48 | 0.26 | 0.28 | 0.10[c] | 3 | ZSM-5 |
| 4[b] | 300 | 48 | 0.26 | 0.28 | 0.10[c] | 1 | ZSM-5 |
| 5[d] | 300 | 48 | 0.26 | 0.28 | 0.20[b] | 1 | ZSM-5 |
| 6[b] | 200 | 48 | 0.26 | 0.30 | 0.10[e] | 4 | ZSM-48 |
| 7[b] | 200 | 48 | 0.26 | 0.30 | 0.10[f] | 4 | ZSM-11 |
| 8[b] | 150 | 48 | 0.26 | 0.31 | 0.10[c] | 2 | ZSM-5 |
| 9[b] | 150 | 48 | 0.26 | 0.31 | 0.10[c] | 2 | ZSM-5 |
| 10[b] | 150 | 48 | 0.26 | 0.31 | 0.10[c] | 2 | ZSM-5 |
| 11[b] | 150 | 48 | 0.26 | 0.31 | 0.10[c] | 3 | ZSM-5 |
| 12[b] | 150 | 48 | 0.26 | 0.31 | 0.10[c] | 2 | ZSM-5 |
| 13[b] | 100 | 48 | 0.26 | 0.34 | 0.08[g] | 3 | ZSM-12 |
| 14[h] | 76 | 48 | 0.26 | 0.59 | 0.10[c] | 6 | ZSM-5 |
| 15[i] | 70 | 40 | 0.20 | 0.23 | 0.10[c] | 3 | ZSM-5 |
| 16[b] | 70 | 48 | 0.26 | 0.37 | 0.10[c] | 3 | ZSM-5 |
| 17[a] | 60 | 48 | 0.26 | 0.39 | 0.10[c] | 3 | ZSM-5 |
| 18[b] | 150 | 40 | 0.20 | 0.25 | 0.10[j] | 3 | ZSM-23 |
| 19[b] | 300 | 40 | 0.20 | 0.23 | 0.10[j] | 3 | ZSM-23 |
| 20[b] | 300 | 40 | 0.20 | 0.23 | 0.10[k] | 3 | ZSM-50 |

[a] Silica source is tetraethylorthosilicate ($Et_4SiO_4$)
[b] Silica source is SPEX Industries precipitated $SiO_2$
[c] R = $TPA^+$
[d] Silica source is DeGussa fumed $SiO_2$
[e] R = DIQUAT-6 = $(CH_3)_3\overset{+}{N}(CH_2)_6\overset{+}{N}(CH_3)_3$
[f] R = $TBA^+$

[g] 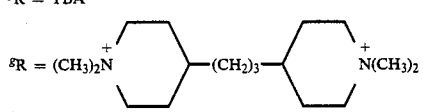
$^gR = (CH_3)_2\overset{+}{N}$-cyclohexyl-$(CH_2)_3$-cyclohexyl-$\overset{+}{N}(CH_3)_2$

[h] Q-brand sodium silicate
[i] Silica source is kieselsaure precipitated $SiO_2$
[j] R = DIQUAT-7 = $(CH_3)_3\overset{+}{N}(CH_2)_7\overset{+}{N}(CH_3)_3$
[k] R = Dibenzyldimethylammonium ion Table 2A is a compilation of chemical analyses of some of our indium-containing products. These products vary in indium content from 0.36–5.20 wt % In. The formulas of the zeolite products are expressed in Table 2 as a ratio of oxides per mole of $In_2O_3$.

The diffraction pattern of Sample of Run No. 8 showed it to be ZSM-5, of Sample from Run No. 13 showed it to be ZSM-12 and of Sample from Run No. 6 showed it to be ZSM-48.

TABLE 2A

| | Analyses of Some Indium-Containing Zeolitic Silicate Products | | | | | | | | | | | |
|---|---|---|---|---|---|---|---|---|---|---|---|---|
| Sample Run from No. | Weight Percent | | | | | | | Moles C Moles N | Moles per Mole $In_2O_3$ | | | |
| | C | N | Na | In | $SiO_2$ | $Al_2O_3$ | Ash | | $N_2O$ | $Na_2O$ | $Al_2O_3$ | $SiO_2$ |
| 15 | 6.96 | 0.66 | 3.28 | 5.20 | 62.47 | 0.070 | 85.34 | 12.3 | 1.04 | 3.15 | 0.03 | 46 |
| 14 | 6.74 | 0.43 | 2.64 | 4.19 | 69.94 | 0.24 | 86.20 | 18.3 | 0.84 | 3.14 | 0.13 | 64 |
| 16 | 7.02 | 0.56 | 0.79 | 3.48 | 76.45 | 0.035 | 84.78 | 14.6 | 1.32 | 1.13 | 0.02 | 84 |
| 13 | 6.01 | 0.61 | 0.65 | 2.79 | 81.83 | 0.031 | 91.79 | 11.2 | 1.79 | 1.16 | 0.025 | 112 |
| 9 | 8.02 | 0.71 | 0.98 | 2.11 | 74.85 | 0.078 | 88.05 | 13.6 | 2.36 | 2.29 | 0.06 | 132 |
| 8 | 8.01 | 0.68 | 1.48 | 2.14 | 74.64 | 0.11 | 88.72 | 13.7 | 2.61 | 3.45 | 0.11 | 133 |
| 12 | 7.93 | 0.74 | 0.56 | 2.26 | 83.85 | 0.005 | 88.05 | 12.4 | 2.68 | 1.23 | 0.009 | 142 |
| 10 | 8.37 | 0.81 | 1.83 | 1.92 | 73.14 | 0.025 | 88.36 | 12.0 | 3.46 | 4.76 | 0.03 | 146 |
| 11 | 8.22 | 0.62 | 0.54 | 1.49 | 82.14 | 0.031 | 85.96 | 15.5 | 3.41 | 1.81 | 0.05 | 211 |
| 6 | 4.58 | 0.79 | 0.48 | 1.46 | 86.70 | 0.029 | 91.86 | 6.7 | 4.44 | 1.64 | 0.045 | 227 |
| 7 | 8.66 | 0.51 | 0.44 | 0.96 | 82.29 | 0.013 | 89.43 | 19.8 | 4.36 | 2.29 | 0.045 | 328 |
| 2 | 8.12 | 0.69 | 0.40 | 0.36 | 78.05 | 0.083 | 85.69 | 13.7 | 15.7 | 5.55 | 0.52 | 830 |

EXAMPLE B

The In/ZSM-5 of that run No. 12 was prepared as follows:

The source of the indium can be incorporated into the zeolitic silicate synthesis reaction mixture as a partial, or preferably as a complete substitute for sources of alumina (or boron) conventially used in zeolite synthesis. In the embodiments described below the crystalline indium containing silicates were synthesized from crystallization reaction mixtures which contained no deliberately added sources of $Al_2O_3$.

A commercial silica gel (SPEX Ind.) with very low aluminum contamination was employed in the synthesis of In-ZSM-5. First, 0.85 g $In(NO_3)_3$ and 2.66 g NaOH pellets were dissolved in 180.2 g de-ionized water, then 5.64 g tetrapropylammonium bromide (TPABr) was dissolved in this basic solution. This solution was transferred to a 300 ml stainless steel autoclave, and 15.0 g of silica gel (SPEX) was added. The autoclave was then sealed and stirring and heating was begun. The hydrogel formed by this reaction mixture is described by the following mole ratios:

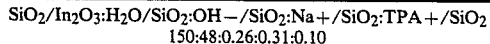
$SiO_2/In_2O_3:H_2O/SiO_2:OH-/SiO_2:Na+/SiO_2:TPA+/SiO_2$
150:48:0.26:0.31:0.10

The hydrogel was reacted at 160° C. for 2 days at a stirring rate of 400 rpm before quenching. The resultant crystalline product was filtered, washed, and dried. X-ray powder diffraction analysis showed the product to be 100% crystalline ZSM-5, when compared to the diffraction pattern of a conventional ZSM-5. Elemental analysis of the ZSM-5 product gave: C=7.93 wgt %, N=0.74%, Na=0.56%, In=2.26%, Al 0.005%, $SiO_2$=83.85%, Ash=88.05%.

These results expressed in mole ratios were: C/N=12.5; Moles/mole $In_2O_3:N_2O$=2.68, $Na_2O$=1.23, $Al_2O_3$=0.009, $SiO_2$=142.

Platinum incorporation was undertaken as follows: The as-synthesized zeolite was heated in nitrogen to 520° C. at 1C/min and held there for 6 hours. It was then calcined in air in a similar manner. The calcined zeolite analyzed for 41.05% Si, 2.21% In (Si/In2=152), and 120 ppm Al, and sorbed 10.4% n-hexane at 90C. The calcined zeolite (3 g) was stirred in a solution of 150 mg $Pt(NH_3)_4Cl_2$ in 100 ml water at room temperature overnight. After being washed, filtered and dried, the ion-exchanged zeolite was found to contain 0.41 meq $NH_3$/g ash, which is equivalent to 1.89% Pt on sample. The platinum tetramine zeolite was then calcined in oxygen to 350C at 0.5C/min and held there for 1 hour.

Elemental analysis indicated the presence of 1.85% Pt on the final catalyst.

A standard test (based on hexane conversion at 1000° F.) indicated a hexane conversion activity between 200 and 500, with a very high benzene selectivity (60%). At very high hexane conversions (99%), benzene was formed in over 94% yield. Similarly, n-heptane yielded 96% toluene. Similarly, n-heptane yielded 96% toluene. Consistent with the non-acidic nature of this platinum catalyst, n-octane yielded predominantly ethylbenzene and ortho-xylene, 2-methylheptane produced mostly meta-xylene, and 3-methylheptane formed mainly ethylbenzene, para-, and ortho-xylene.

EXAMPLE C

In EXAMPLE A, zeolitic silicate was made using $In(NO_3)_3$ in the crystallization reaction mixture as in the Example below. Here, indium was incorporated post-synthesis; in a subsequent step platinum was ion-exchanged onto the zeolite.

In this example, a high silica/alumina (10,000) ZSM-11 was calcined in nitrogen and then in air at 538° C. $InCl_3$ vapors were passed through the zeolite in a stream of nitrogen, while it was heated to 500° C. at 10C/min. The zeolite was maintained at 500° C. for 1.5 hours. After cooling, the catalyst was added to 200 ml 1M $NH_4Cl$ adjusted to pH 9.5 with $NH_4OH$. The mixture was stirred for 20 minutes at room temperature, and the filtered. The zeolite was then reexchanged for 3 hours with 1M $NH_4Cl$ adjusted to pH 7.6. Thermogravimetric analysis indicated the presence of 0.325 meg/g ammonium ion in the zeolite.

Platinum was incorporated by ion exchange with $Pt(NH_3)_4Cl_2$ at room temperature. The platinum zeolite was then calcined in oxygen to 350C at 0.5C/min.

The "non-acidic" nature of the catalyst was confirmed by its ability to aromatize n-heptane to toluene in high yield. At about 500° C. (up t about 538° C.) and 30 torr heptane in nitrogen, toluene was formed in 94% selectivity at a conversion level of greater than 90%.

EXAMPLE D

The ZSM-5-type borosilicate was synthesized at 170° C. from a mixture of 12.4 g high purity silica (SPEX), 105 g 20% TEA hydroxide, and 0.8 g boric acid. The as-synthesized zeolite was then calcined in nitrogen and then in air at 520° C. The calcined zeolite contained 41.39% Si, 0.015% Al, and 0.44% B.

Two grams of the calcined borosilicate was impregnated with 135 mg $In(NO_3)_3$, and calcined in air at 500° C. for 2 hours. 1.8 g of this material was then ion-exchanged with 28 mg Pt(NH$_3$)$_4$Cl$_2$ in 100 ml water at room temperature. TGA analysis in hydrogen indicated the presence of 0.18 meq N/g equivalent to 0.87% Pt. The platinum-exchanged zeolite was then calcined in oxygen to 350° C. at 0.5° C./min.

The catalyst activity of the foregoing composition was examined. The "non-acidic" nature of the catalyst was confirmed by its ability to aromatize n-heptane to toluene in high yield. At 500° C. and 30 torr heptane in nitrogen, toluene was formed in 95% yield. Furthermore, the small amounts of both methane and propane produced were exceeded by the ethane formed, indicative of the low hydrogenolysis and acid activity of the catalyst.

| % Conversion | % C1 | % C2 | % Benzene | % Toluene (Selectivity) |
|---|---|---|---|---|
| 96 | 0.4 | 0.6 | 1.3 | 92 (96%) |
| 99 | 0.5 | 1.0 | 1.5 | 95 (96%) |

Table 2A is a compilation of chemical analyses of some of our indium-containing zeolitic products. These products vary in indium content from 0.36–5.20 wt % In. The formulas of the zeolite products are expressed in Table 2 as a ratio of oxides per mole of In$_2$O$_3$.

EXAMPLE E

Indium-containing zeolite ZSM-20 was synthesized by the following procedure:

12.75 grams of sodium aluminate (NaAlO$_2$) and 6.02 grams indium nitrate were dissolved in 57.96 grams of deionized water. After the solid ingredients dissolved, 484.1 ml of 2.88 N tetraethylammonium hydroxide (TEAOH) was added to the solution. The resulting solution was not styirred into 312.5 grams of tetraethylorthosilicate. This solution was kept stirring for one hour until the hydrolysis reaction was complete. The resulting hydrogel was now transferred to a one-liter polypropylene bottle.

The polypropylene bottle was loosely capped and placed into a steambox (100° C.) to promote the crystallization of the zeolite. The next morning the bottle was removed from the steambox and the bottle cap was now closed tightly. The bottle was shaken vigorously, then replaced into the steambox. The reaction mixture for the initial hydrogel formed for the synthesis of the indium-containing ZSM-20 can be described by the following set of mole ratios:

| SiO$_2$/In$_2$O$_3$ | 150 |
|---|---|
| H$_2$O/SiO$_2$ | 10 |
| OH$^-$/SiO$_2$ | 0.9 |
| Na$^+$/SiO$_2$ | 0.09 |
| TEA$^+$/SiO$_2$ | 0.93 |
| SiO$_2$/Al$_2$O$_3$ | 30 |

Samples of the solid product were removed daily from the polypropylene bottle for X-ray diffraction (XRD) analysis to determine the product crystallinity. XRD analysis showed that the ZSM-20 crystallization was complete in 14 days. The polypropylene bottle was removed from the steambox, and the solid product was filtered on a Büchner funnel. After filtration, the product zeolite was boiled in de-ionized water and again filtered and dried under an infrared heat lamp. After drying, a sample of the product was submitted for XRD and chemical analysis. XRD analysis showed the product to be zeolite ZSM-20. The chemical analysis for the indium-containing ZSM-20 was:

| Weight Percent | | | | | | |
|---|---|---|---|---|---|---|
| C | N | Na | In | SiO$_2$ | Al$_2$O$_3$ | Ash |
| 10.0 | 1.2 | 3.0 | 3.08 | 58.5 | 11.4 | 75.1 | which gives:

| Moles C | Moles per Mole In$_2$O$_3$ |
|---|---|
| Moles N | N$_2$O:Na$_2$O:Al$_2$O$_3$:SiO$_2$ |
| 9.7 | 3.19:4.86:8.33:72.7 |

EXAMPLE F

Indium-containing zeolite Beta was synthesized in the following manner:

5.95 grams of sodium aluminate and 4.68 grams of indium nitrate were dissolved in 85.14 grams of de-ionized water. After the salts dissolved, 105.0 ml of 3.1 N TEAOH was added to the solution. The resulting solution was transferred to a 300 ml stainless-steel autoclave.

Now 46.67 grams of solid silica gel (SPEX Industries) was pored into the autoclave, the autoclave was sealed and stirring and heating begun immediately. The reaction was carried out at 160° C. with stirring (400 rpm).

The initial reaction mixture for the synthesis of indium-containing zeolite Beta can be described by the mole ratios:

| SiO$_2$/In$_2$O$_3$ | 90 |
|---|---|
| H$_2$O/SiO$_2$ | 12 |
| OH$^-$/SiO$_2$ | 0.40 |
| Na$^+$/SiO$_2$ | 0.09 |
| TEA$^+$/SiO$_2$ | 0.46 |
| SiO$_2$/Al$_2$O$_3$ | 30 |

After 4 days the autoclave was quenched in a water plus ice bath to terminate the reaction. The solid product was filtered, boiled in water and again filtered. XRD analysis showed the crystalline product to be zeolite Beta. Chemical analysis of the indium-containing zeolite Beta product gave the following results:

| Weight Percent | | | | | | |
|---|---|---|---|---|---|---|
| C | N | Na | In | SiO$_2$ | Al$_2$O$_3$ | Ash |
| 10.84 | 1.71 | 1.4 | 2.5 | 69.8 | 4.2 | 79.92 | which gives:

| Moles C | Moles per Mole In$_2$O$_3$ |
|---|---|
| Moles N | N$_2$O:Na$_2$O:Al$_2$O$_3$:SiO$_2$ |
| 7.4 | 5.61  2.79  3.78  62.8 |

EXAMPLE G

Indium-containing crystalline aluminophosphate molecular sieve ALPO-5 was synthesized as follows:

23.1 grams of concentrated phosphoric acid (86.3% H$_3$PO$_4$) was diluted with 30.0 grams of de-ionized water. Now 10.0 grams of Kaiser alumina was stirred into this acid solution and the mixture was digested for 45 minutes at 90° C. with continuous stirring. After the digestion period a solution containing 1.18 grams of indium nitrate dissolved in 41.0 grams of de-ionized water was stirred into the gel. Finally, 37.0 grams of 40% wt. TEAOH solution was stirred into the gel and stirring continued until a uniform gel was produced. This gel was not transferred to a 300 ml stainless-steel autoclave. The resulting reaction mixture hydrogel can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $TEA^+/Al_2O_3$ | 1.0 |

The autoclave was sealed and heated and stirring began immediately. The reaction was carried out at 160° C. with stirring (400 rpm).

After 4 days the autoclave was quenched in a water-+ice bath to terminate the crystallization. The solid product was filtered, boiled in water and filtered again. After drying the product, XRD analysis showed the material to be crystalline aluminophosphate designated by Union Carbide as ALPO-5. Chemical analysis of the indium-containing ALPO-5 gave:

| Weight Percent | | | | | | |
|---|---|---|---|---|---|---|
| C | N | Na | P | Al | In | Ash |
| 6.66 | 0.84 | 0.48 | 21.05 | 16.01 | 1.44 | 89.45 |
| which gives: | | | | | | |
| Moles C | | | Moles per Mole $In_2O_3$ | | | |
| Moles N | | | $N_2O:Na_2O:P_2O_5:Al_2O_3$ | | | |
| 9.2 | | | 4.78  1.66  54.2  47.3 | | | |

EXAMPLE H

Indium-containing crystalline silicoaluminophosphate molecular sieve SAPO-5 was synthesized in a manner analogous to EXAMPLE G:

46.2 grams of concentrated phosphoric acid (86.3% $H_3PO_4$) was first diluted with 60.0 grams of de-ionized water then 20.0 grams of Kaiser alumina was added to the solution. This mixture was now digested on a hot plate at 90° C. for 45 minutes, with continuous stirring. At the end of the digestion period, a solution containing 2.36 grams of indium nitrate dissolved in 82.0 grams of de-ionized water was stirred into the gel. Next 74.0 grams of 40% wt TEAOH solution was stirred into the gel. This mixture was now stirred at room temperature until a uniform hydrogel was produced. The resulting hydrogel was transferred to a one-liter stainless-steel autoclave. Before sealing the autoclave, 2.04 grams of tetraethylorthosilicate was transferred to the autoclave. The autoclave was then sealed and heating and stirring was begun immediately. The resulting reaction mixture can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $SiO_2/Al_2O_3$ | 0.10 |
| $TEA^+/Al_2O_3$ | 1.0 |

The crystallization of the indium-containing SAPO was carried out at 150° C. with stirring (400 rpm).

At the end of 4 days the autoclave was quenched in a water+ice bath to terminate the crystallization. The solid product was filtered, boiled in water, and re-filtered. After drying under a heat lamp, XRD analysis showed that the reflection lines for the product corresponded to silicoaluminophosphate SAPO-5, a Union Carbide designation for this material.

Chemical analysis of the indium-containing SAPO-5 gave:

| Weight Percent | | | | | | | |
|---|---|---|---|---|---|---|---|
| C | N | Na | P | Al | In | Si | Ash |
| 6.32 | 0.60 | 0.48 | 19.88 | 15.71 | 1.45 | 0.66 | 85.00 |
| | | | which gave | | | | |
| Moles C | | | Moles per Mole $In_2O_3$ | | | | |
| Moles N | | | $N_2O:Na_2O:P_2O_5:Al_2O_3:SiO_2$ | | | | |
| 12.3 | | | 3.39  1.65  50.8  46.1  3.7 | | | | |

EXAMPLE I

Platinum incorporation into the indium-containing silicate of ZSM-5 structure was carried out by direct addition of a platinum compound to the zeolite synthesis reaction mixture as follows:

A solution was prepared by dissolving 2.00 grams of indium nitrate and 13.07 grams of NaOH pellets in 710.28 grams of de-ionized water. After the solids dissolved, 26.6 grams of tetrapropylammonium bromide (TPABr) was dissolved in the solution. Finally 1.29 grams of platinum tetraaminenitrate $[Pt(NH_3)_4(NO_3)_2]$ as dissolved in the solution, and the solution was transferred to a one-liter stainless-steel autoclave. Before sealing the autoclave, 66.67 grams of commercial silica gel (SPEX Industries) was poured into the autoclave. The autoclave was then sealed and heating and stirring was begun immediately. The reaction mixture hydrogel can be described by the following mole ratios:

| | |
|---|---|
| $SiO_2/In_2O_3$ | 300 |
| $H_2O/SiO_2$ | 40 |
| $OH^-/SiO_2$ | 0.30 |
| $Na^+/SiO_2$ | 0.33 |
| $TPA^+/SiO_2$ | 0.10 |
| $SiO_2/Pt$ | 300 |

The crystallization was carried out at 170° C. with stirring (400 rpm).

After 4 days the autoclave was quenched in a water-+ice bath to terminate the crystallization. In the usual manner the solid product was filtered, boiled in water, and finally filtered again before drying under a heat lamp. XRD analysis of the solid product showed the material to be crystalline zeolite ZSM-5.

Chemical analysis of the indium-containing ZSM-5 product gave:

| Weight Percent | | | | | | | | |
|---|---|---|---|---|---|---|---|---|
| C | N | Na | In | Pt | $SiO_2$ | $Al_2O_3$ | Ash | |
| 8.27 | 0.74 | 1.3 | 1.1 | 0.52 | 82.7 | 0.0265 | 85.05 | |
| | | | which gave: | | | | | |
| Moles C | | | Moles per Mole $In_2O_3$ | | | | | |
| Moles N | | | $N_2O:Na_2O:Al_2O_3:SiO_2:Pt$ | | | | | |
| 13.1 | | | 5.52  5.90  0.05  288  0.55 | | | | | |

EXAMPLE J

A boron-containing zeolite beta was synthesized and then calcined to remove the organic template, by heating first in $N_2$ 25°–530° at 10/min and held 6 hrs. then in air in $N_2$ 25°–530° at 10/min. and held 6 hours.

25 g of the calcined zeolite was ion-exchanged with 750 mg $Pt(NH_3)_4Cl_2$ in 400 ml $H_2O$ at room temperature overnight. The dried material was then calcined in flowing oxygen (100 cc/min.) 25°-350° at ½°/min. and held 1 hour.

10 g of the calcined Pt-containing zeolite was then treated with 0.9 g In(NO$_3$)$_3$H$_2$O in 200 ml H$_2$O at room temperature overnight.

The zeolite was filtered and washed.

The In-containing Pt/zeolite was added to 150 ml H$_2$O and titrated to pH 9.0 with 0.5M CsOH (1½ hrs). The material was filtered, washed, and dried. The final product contained 0.76% Pt, 11% Cs, 1.1% In, and 0.08% B.

EXAMPLE K

The synthesis of a binary oxide zeolite having the structure of ZSM-5 was carried out in the two-phase system as in Ser. No. 878,555 filed June 26, 1986. The aqueous phase of the two-phase system comprised 2.8 g In(NO$_3$)$_3$xH$_2$O dissolved in 35 g water to which was added 63 g TPAOH (40% in H$_2$O). Constituting the organic phase was 77.0 g Si(OCH$_3$)$_4$ dissolved in 35 g of 1-hexanol. The mixture was nucleated at 180° C. for 24 hours and crystallized at 200° C. for 144 hours. The final product was filtered and washed. The X-ray diffraction pattern of the dried material proved it to be well-crystallized ZSM-5.

The sample was ammonium-exchanged (1M NH$_4$Cl, twice, 60° C., 20 ml/g zeolite) and calcined. The chemical composition of the ash of a 1000° C. calcined sample was 79.3 wt. % SiO$_2$ and 1.5 wt. % In$_2$O$_3$. The ash residue also contained a small quantity, i.e. 85 ppm, of aluminum.

Temperature-programmed desorption of ammonia indicated an exchange capacity of 0.09 meq/g for the product of this example. The Si/In ratio from TPAD was 190.5. The sample had an Alpha Value of 1.0.

The particle size of the product from this example was about 0.2 microns. The particles were made of pure single crystals with almost cubic appearance.

EXAMPLE L

The synthesis of Example K was repeated, except that the mixture contained 3.6 g In(NO$_3$)$_3$xH$_2$O in the aqueous phase. The product material was filtered and dried. It had the same characteristic ZSM-5 X-ray lines as the product of Example K. The material was calcined and ammonium-exchanged as described in Example K. The chemical composition of the ash of a 1000° C. calcined sample was 78.2 wt. % SiO$_2$ and 3.1 wt. % In$_2$O$_3$. The ash residue also contained a small quantity, i.e. 180 ppm, of aluminum.

Temperature-programmed desorption of ammonia indicated an exchange capacity of 0.21 meq/g for the product of this example. The Si/In ratio from TPAD was 77.9. The sample had an Alpha Value of 2.5.

The particle size of the product from this example was about 0.2 microns. The particles were made of crystals with almost cubic appearance. There were no impurities present.

EXAMPLES M-Q

The synthesis of Example K was repeated, except that the mixtures contained varying amounts of In(NO$_3$)$_3$.xH$_2$O. Five preparations were made, with the following compositions:

| Example | M | N | O | P | Q |
|---|---|---|---|---|---|
| Aqueous Phase (g) | | | | | |
| H$_2$O | 40.0 | 40.0 | 35.0 | 40.0 | 40.0 |
| In(NO$_3$)$_3$ × 3H$_2$O | 0.9 | 7.2 | 1.8 | 1.8 | 3.6 |
| TPAOH, 40% | 63.0 | 63.0 | 63.0 | 63.0 | 63.0 |
| Organic Phase (g) | | | | | |
| 1-Hexanol | 60.0 | 60.0 | 35.0 | 60.0 | 60.0 |
| Si(OCH$_3$)$_4$ | 77.0 | 77.0 | 77.0 | 77.0 | 77.0 |

The product materials were filtered and dried. They had the same characteristic X-ray lines as ZSM-5. The materials were calcined and ammonium-exchanged as in Example K. Their properties were as follows:

| Example | M | N | O | P | Q |
|---|---|---|---|---|---|
| SiO$_2$, wt. % | 84.0 | 77.5 | 80.5 | 76.7 | 82.5 |
| In$_2$O$_3$, wt. % | 0.67 | 5.1 | 1.58 | 1.31 | 2.92 |
| Al ppm | 105 | 65 | 130 | 85 | 60 |
| Exchange Capacity meq/g | 0.09 | 0.17 | 0.17 | 0.12 | 0.21 |
| Si/In (from TPAD) | 193 | 99 | 95 | 138 | 77 |
| Alpha Value | 1.5 | 1.6 | 1.0 | 1.0 | n.d. |
| Particle size | 2000A | 1 micr | 2000A | 2000A | 2000A |

What is claimed is:

1. A catalytic dewaxing process comprising contacting a waxy feed, containing C$_{15}$+ paraffins, under dewaxing conditions, with a catalyst consisting of a dehydrogenation metal and a non-acidic crystalline microporous indium-containing material;
    dewaxing said C$_{15}$+ paraffins to
    a product having a pour point which is less than that of the feed.

2. The process of claim 1, wherein said dewaxing conditions include a temperature ranging from about 500 to 1200° F.; a pressure ranging from 0 to 1000 psig; a weight hourly space velocity of 0.1 to 20; and H$_2$:feed ratio of 0 to 20:1.

3. The process of claim 1, wherein said non-acid microporous crystalline indium-containing material include 0.05 to 20 weight percent indium and wherein the dehydrogenation metal comprises 0.01 to 30 weight percent of the catalyst composition.

4. The process of claim 1, wherein said non-acidic crystalline microporous indium-containing material exhibits the X-ray diffraction pattern of a zeolite selected from the group consisting of ZSM-5, ZSM-11, ZSM-12, ZSM-23, ZSM-48, ZSM-50 and zeolite Beta.

5. The process of claim 1, wherein said non-acidic crystalline microporous indium-containing material contains cations selected from the group consisting of Periodic Table Group IA and IIA cations.

6. The process of claim 1, wherein prior to said contacting said feed is subjected to conventional hydrotreating conditions to remove therefrom any one of the elements selected from the group consisting of sulfur, nitrogen and oxygen, said elements present as hydrocarbon derivatives of components of the feed.

7. The process of claim 1, wherein the dehydrogenation metal is a platinum group metal.

8. The process of claim 1, wherein the dehydrogenation metal is platinum.

9. The process of claim 4, wherein the dehydrogenation metal is platinum.

* * * * *